(12) United States Patent
Omuro et al.

(10) Patent No.: US 9,423,347 B2
(45) Date of Patent: Aug. 23, 2016

(54) AUTOMATIC ANALYZING APPARATUS

(75) Inventors: Naoko Omuro, Koshigaya (JP); Shoichi Kanayama, Otawara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 185 days.

(21) Appl. No.: 12/365,414

(22) Filed: Feb. 4, 2009

(65) Prior Publication Data

US 2009/0196793 A1   Aug. 6, 2009

(30) Foreign Application Priority Data

Feb. 6, 2008   (JP) .................................. 2008-026526
Jan. 7, 2009   (JP) .................................. 2009-001458

(51) Int. Cl.
| | | |
|---|---|---|
| G01N 21/00 | (2006.01) | |
| B01F 3/00 | (2006.01) | |
| B01F 13/08 | (2006.01) | |
| G01N 21/59 | (2006.01) | |
| B01F 11/00 | (2006.01) | |
| G01N 35/02 | (2006.01) | |
| G01N 35/00 | (2006.01) | |

(52) U.S. Cl.
CPC ........ *G01N 21/5907* (2013.01); *B01F 11/0082* (2013.01); *B01F 11/0091* (2013.01); *G01N 35/025* (2013.01); *G01N 2035/00534* (2013.01)

(58) Field of Classification Search
CPC ............. B01F 11/0082; B01F 11/0091; B01F 13/0818; G01N 2035/00534
See application file for complete search history.

(56) References Cited

U.S. PATENT DOCUMENTS

| | | | | |
|---|---|---|---|---|
| 3,399,869 A | * | 9/1968 | Jerome Suhre et al. ...... | 366/112 |
| 3,645,506 A | * | 2/1972 | Selesnick ............ | B01F 13/0818 |
| | | | | 366/273 |
| 4,732,487 A | * | 3/1988 | Pollard ......................... | 366/112 |
| 5,725,500 A | * | 3/1998 | Micheler ......................... | 604/82 |
| 6,357,907 B1 | * | 3/2002 | Cleveland ........... | B01F 13/0818 |
| | | | | 366/273 |
| 2002/0182110 A1 | * | 12/2002 | Behnk ............................ | 422/72 |
| 2005/0127215 A1 | * | 6/2005 | Lienhart et al. ................. | 241/21 |
| 2005/0238540 A1 | * | 10/2005 | Swon ................. | B01F 11/0082 |
| | | | | 422/561 |

FOREIGN PATENT DOCUMENTS

| | | | |
|---|---|---|---|
| JP | 56-137732 A | 10/1981 | |
| JP | 60-58235 A | 4/1985 | |
| JP | 2-234532 A | 9/1990 | |
| JP | 4-271823 | 9/1992 | |

(Continued)

OTHER PUBLICATIONS

Office Action issued Oct. 30, 2012, in Japanese Patent Application No. 2009-001458 (English Translation only).

*Primary Examiner* — P. Kathryn Wright
(74) *Attorney, Agent, or Firm* — Oblon, McClelland, Maier & Neustadt, L.L.P.

(57) ABSTRACT

An automatic analyzing apparatus includes a stir piece moving part that moves a stir piece for stirring a mixture into a reaction container, a reaction disk that rotationally moves and thereafter stops the reaction container in which the stir piece moved by the stir piece moving part and the mixture are housed, and first drivers that drive the stir piece in the reaction container to stir first and second mixtures. During the rotation movement of the reaction container into which first and second reagents have been dispensed at first and second reagent dispensing positions, the first drivers vertically move the stir piece in the reaction container and stir the first and second mixtures.

5 Claims, 10 Drawing Sheets

(56) References Cited

FOREIGN PATENT DOCUMENTS

| JP | 8-178931 | | 7/1996 |
| JP | 08-201395 | * | 8/1996 |
| JP | 9-99034 A | | 4/1997 |
| JP | 2000-254472 | | 9/2000 |

* cited by examiner

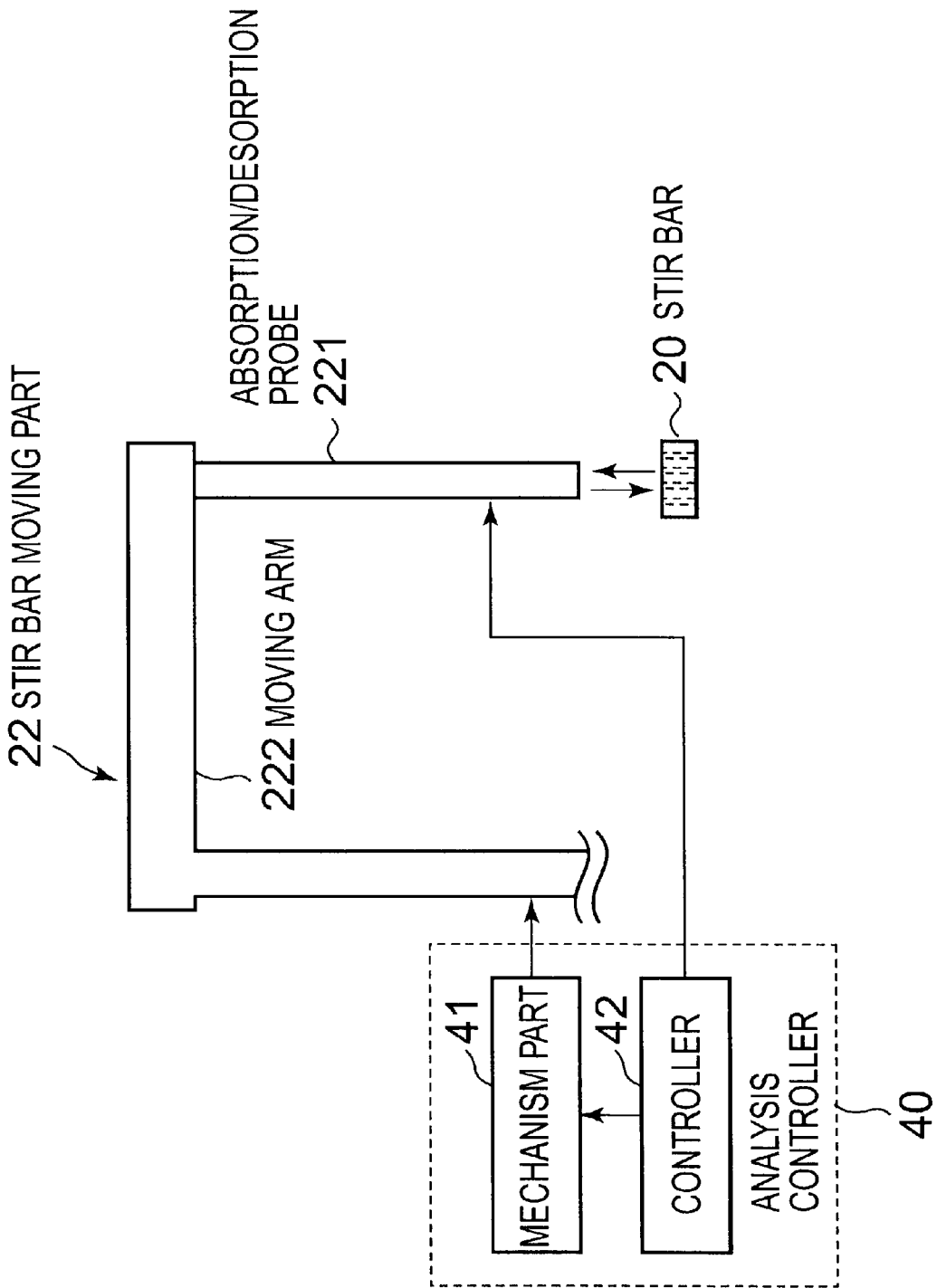

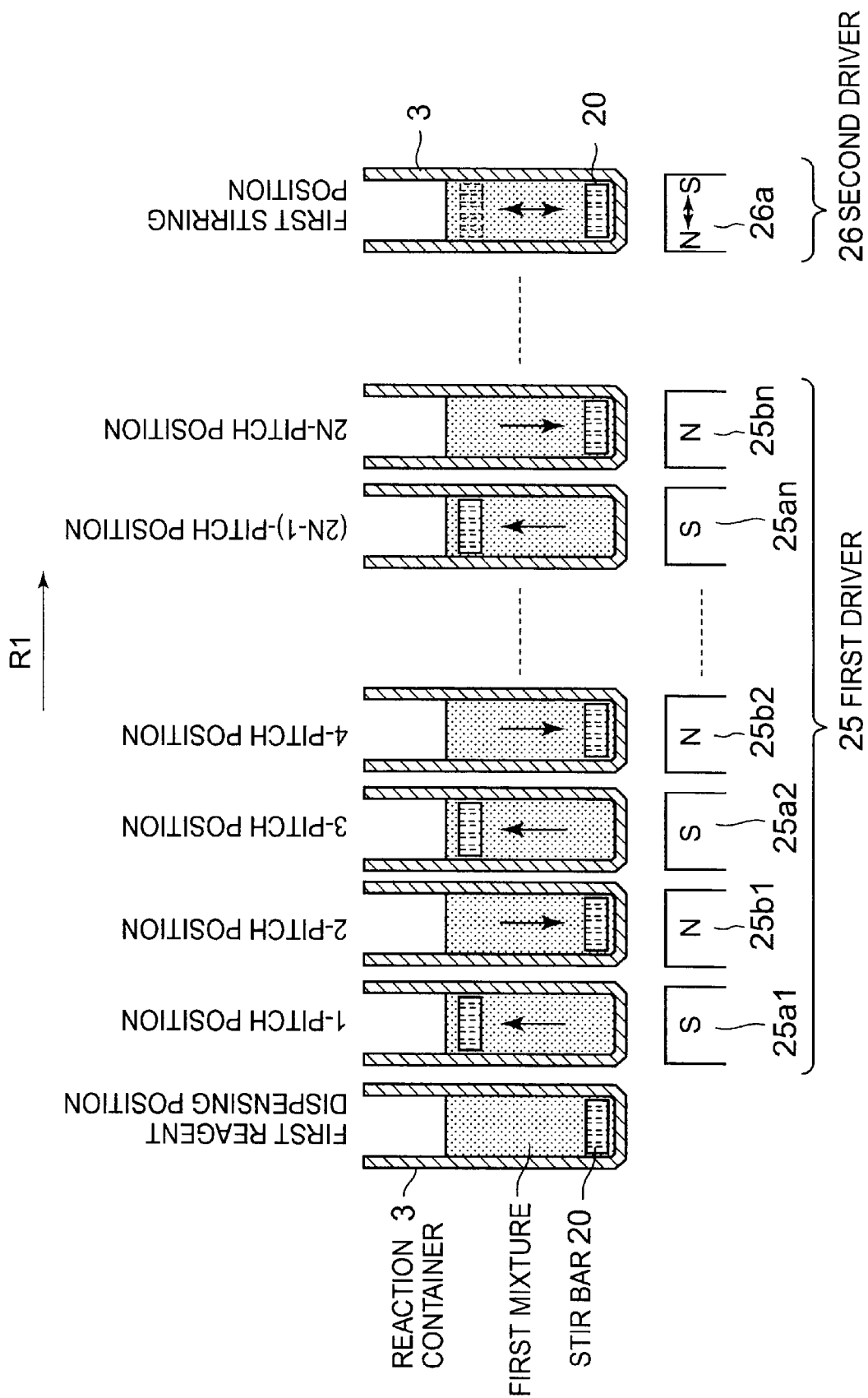

FIG. 10

63 ANALYSIS CONDITION SETTING SCREEN

| | | |
|---|---|---|
| ITEM NAME | AST ▼ | ~631 |
| SAMPLE AMOUNT | 5 | ~632 |
| REAGENT AMOUNT  FIRST REAGENT | 150 | ~633 |
| SECOND REAGENT | 50 | ~634 |
| WAVELENGTH  WAVELENGTH 1 | 340 ▼ | ~635 |
| WAVELENGTH 2 | 380 ▼ | ~636 |
| PHOTOMETRIC POINT | 20 ▼ ~ 29 ▼ | 637 / ~638 |

AUTOMATIC ANALYZING APPARATUS

BACKGROUND OF THE INVENTION

1. Field of the Invention

The present invention relates to an automatic analyzing apparatus that analyzes components contained in fluid and a stirring method thereof, more specifically, relates to an automatic analyzing apparatus that analyzes chemical components contained in blood, urine, etc., of human.

2. Description of the Related Art

An automatic analyzing apparatus covers biochemical test items and immunoserological test items. The automatic analyzing apparatus dispenses a test sample and a reagent corresponding to a test item for the test sample into a reaction container, and measures the change in color tone and turbidity due to reaction of a mixture by measurement of transmission light, thereby obtaining the densities and enzyme activities of various components in the test sample.

This automatic analyzing apparatus measures a test item selected for a test from among a plurality of test items that are measurable based on the setting of analysis conditions for each test sample. When the rotationally moving reaction container stops, a sample-and-reagent dispensing probe dispenses the sample and a reagent for the test item into the reaction container. After the sample and the reagent are dispensed, a stir piece stirs the mixture of the sample and the reagent in the reaction container when the reaction container stops. After the mixture is stirred, a photometric part measures the mixture in the rotationally moving reaction container. The sample-and-reagent dispensing probe is cleaned every time dispensing ends, the stir piece is cleaned every time stirring ends, and the reaction container is cleaned every time mixture measurement ends. The sample-and-reagent dispensing probe, the stir piece, and the reaction container are repeatedly used for measurement every time cleaning ends.

Meanwhile, a method for stirring a mixture is, for example, moving a stir piece attached to the tip of a motor from above into a reaction container while the reaction container is stopping, and rotating the stir piece to stir a mixture in the reaction container. Moreover, a method of moving a stir piece disposed to the tip of a thin metal plate, on whose both faces piezoelectric elements are bonded, from above into a reaction container and vibrating the stir piece to stir a mixture in the reaction container is also known (Japanese Patent No. 3135605).

However, the automatic analyzing apparatus required to process a number of tests (obtained by multiplying the number of test samples by the number of test items) at high speeds cannot sufficiently stir a mixture while a reaction container is stopping in a case where, for example, the mixture contains a test sample or reagent with high viscosity. Consequently, a problem of deterioration of analysis data arises.

SUMMARY OF THE INVENTION

The present invention has been devised to solve the above problem, and makes it possible to increase the stir performance. An object of the present invention is to provide an automatic analyzing apparatus and a stirring method thereof that can prevent deterioration of analysis data due to insufficient stir.

In a first aspect of the present invention, an automatic analyzing apparatus comprises: a stir piece housed so as to be vertically movable in a reaction container housing a mixture of a test sample and a reagent; a reaction container moving part configured to move the reaction container housing the stir piece and the mixture; and a driver configured to stir the mixture by alternately driving the stir piece in the reaction container upward and downward during movement of the reaction container by the reaction container moving part.

According to the first aspect, the mixture is stirred during the movement of the reaction container. Therefore, it is possible to respond to a request for processing a number of tests at high speeds. Moreover, since the stir piece is alternately driven upward and downward, the test sample does not accumulate on the bottom of the reaction container but mixes with the reagent. Therefore, it becomes possible to increase the stir performance, and prevent deterioration of analysis data due to insufficient stir.

Further, in a second aspect of the present invention, an automatic analyzing apparatus comprises: a stir piece, which is a permanent magnet, housed so as to be vertically movable in a reaction container housing a mixture of a test sample and a reagent; and a driver placed below the reaction container, provided with a magnet whose facing plane is formed so as to be capable of facing the reaction container, and configured to relatively move the reaction container and the facing plane of the magnet so that the facing plane of the magnet indicates either an north pole or a south pole to draw the stir piece downward and the facing plane of the magnet indicates the other pole to repulse the stir piece upward.

According to the second aspect, the stir piece is alternately driven upward and downward. Therefore, it becomes possible to increase the stir performance, and prevent deterioration of analysis data due to insufficient stir. Moreover, use of a magnet as the stir piece makes it possible to vertically drive the stir piece by magnetic power with efficiency, and moreover, it becomes possible to install the driver in a small space.

Further, in a third aspect of the present invention, the automatic analyzing apparatus according to the first aspect has a photometric part configured to apply light to the reaction container and measure light transmitted through the mixture in the reaction container. A lower face and an upper face of the stir piece have similar shapes smaller than a bottom face inside the reaction container open-topped and formed into a hollow cylindrical column or polygonal column. A part of a side face of the stir piece facing an inner wall of the reaction container transmitting light is contracted so as not to contact the inner wall.

Further, in a fourth aspect of the present invention, the automatic analyzing apparatus according to the second aspect has a photometric part configured to apply light to the reaction container and measure light transmitted through the mixture in the reaction container. A lower face and an upper face of the stir piece have similar shapes smaller than a bottom face inside the reaction container open-topped and formed into a hollow cylindrical column or polygonal column. A part of a side face of the stir piece facing an inner wall of the reaction container transmitting light is contracted so as not to contact the inner wall.

Further, in a fifth aspect of the present invention, the automatic analyzing apparatus according to the first aspect has at least one piercing hole that pierces the lower face and the upper face so that the mixture in the reaction container can flow from a lower side of the lower face to an upper side of the upper face and vice versa when the stir piece vertically moves in the reaction container.

Further, in a sixth aspect of the present invention, the automatic analyzing apparatus according to the second aspect has at least one piercing hole that pierces the lower face and the upper face so that the mixture in the reaction container can flow from a lower side of the lower face to an upper side of the upper face and vice versa when the stir piece vertically moves in the reaction container.

Further, in a seventh aspect of the present invention, the automatic analyzing apparatus according to the second aspect is characterized in that the magnet is placed on part of an orbit on which the reaction container moves.

Further, in an eighth aspect of the present invention, the automatic analyzing apparatus according to the second aspect is characterized in that the magnet of the driver is an electromagnet.

Further, in a ninth aspect of the present invention, an automatic analyzing apparatus comprises: a stir piece, which is a permanent magnet, housed so as to be vertically movable in a reaction container housing a mixture of a test sample and a reagent; an electromagnet configured to alternately drive the stir piece in the reaction container upward and downward; an electric power supplying part configured to supply an electric current whose polarity is alternately changed to the electromagnet; and a controller configured to control the electric power supplying part based on a liquid property or an amount of one or both of the test sample and the reagent contained in the mixture in the reaction container, and vary a level or frequency of the electric current supplied to the electromagnet or a level and frequency of the electric current supplied to the electromagnet.

According to the ninth aspect, in accordance with the liquid property or the amount of one or both of the test sample and the reagent container in the mixture in the reaction container, the number of times and speed of stir of the mixture is varied. Therefore, it becomes possible to increase the stir performance, and prevent deterioration of analysis data due to insufficient stir. Moreover, it becomes possible to install the driver in a small space.

BRIEF DESCRIPTION OF THE DRAWINGS

FIG. 7 is a view showing the configuration of a stir piece moving part in the embodiment of the present invention.

FIG. 9 is a view showing the configuration of first and second drivers in the embodiment of the present invention.

FIG. 10 is a view showing an example of an analysis condition setting screen displayed on a display in the embodiment of the present invention.

DETAILED DESCRIPTION OF THE EMBODIMENTS (Configuration)

An embodiment of an automatic analyzing apparatus according to the present invention will be described below with reference to FIGS. 1 to 12.

Figure 1:
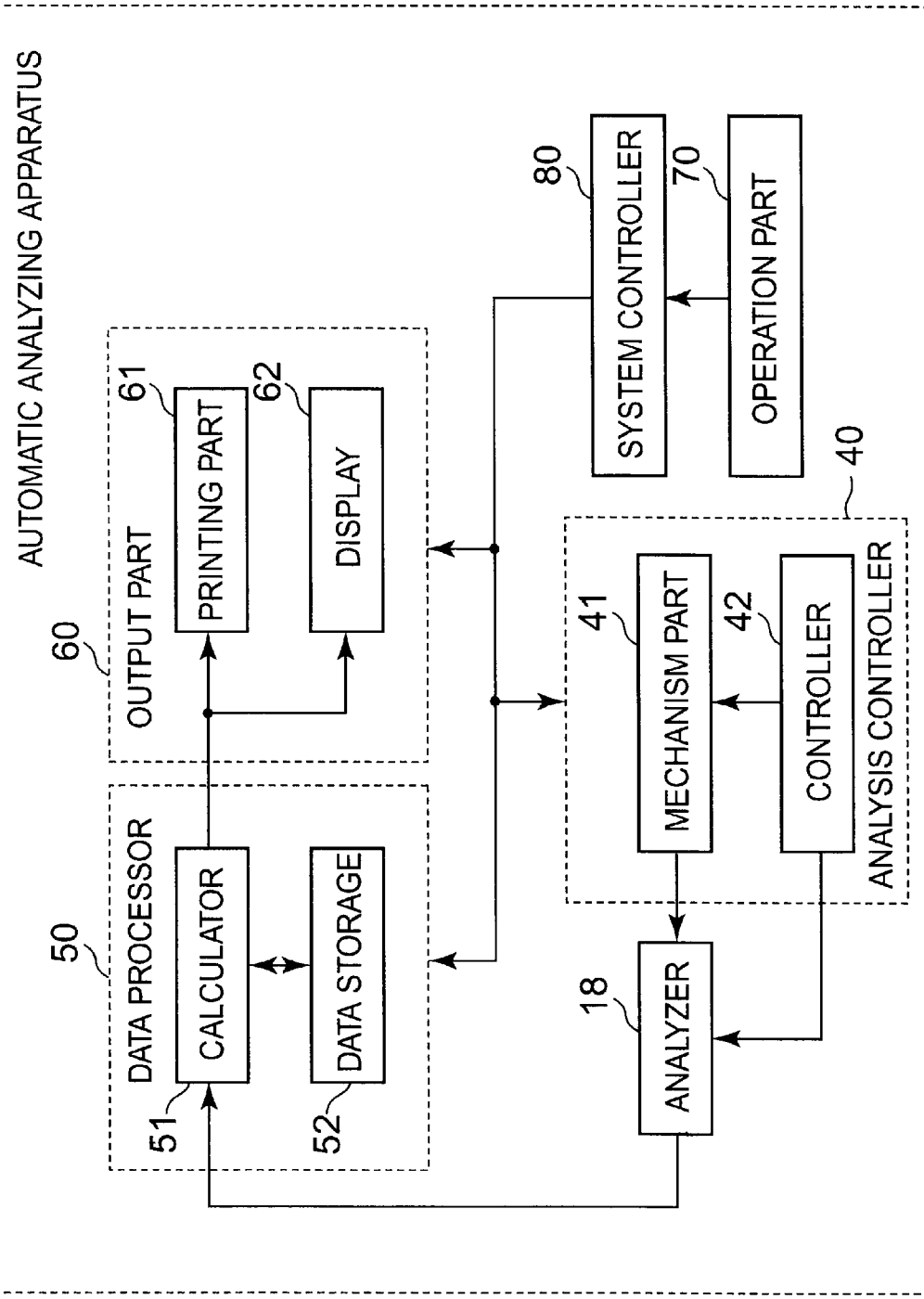
FIG. 1 is a block diagram showing the configuration of an automatic analyzing apparatus according to an embodiment of the present invention.

FIG. 1 is a block diagram showing the configuration of the automatic analyzing apparatus according to the embodiment of the present invention. An automatic analyzing apparatus 100 is provided with: an analyzer 18 configured to measure standard samples or test samples of various test items by using a reagent for every test item; an analysis controller 40 configured to drive and control each unit used in measurement by the analyzer 18; and a data processor 50 configured to process standard sample data or test sample data outputted from the analyzer 18 after measurement of the standard samples or the test samples to create a calibration curve or generate analysis data.

Further, the automatic analyzing apparatus 100 is provided with: an output part 60 configured to output the calibration curve created by the data processor 50 or the analysis data generated thereby; an operation part 70 for inputting analysis conditions for the respective test items, various command signals, etc.; and a system controller 80 configured to integrally control the analysis controller 40, the data processor 50, and the output part 60.

Figure 2:
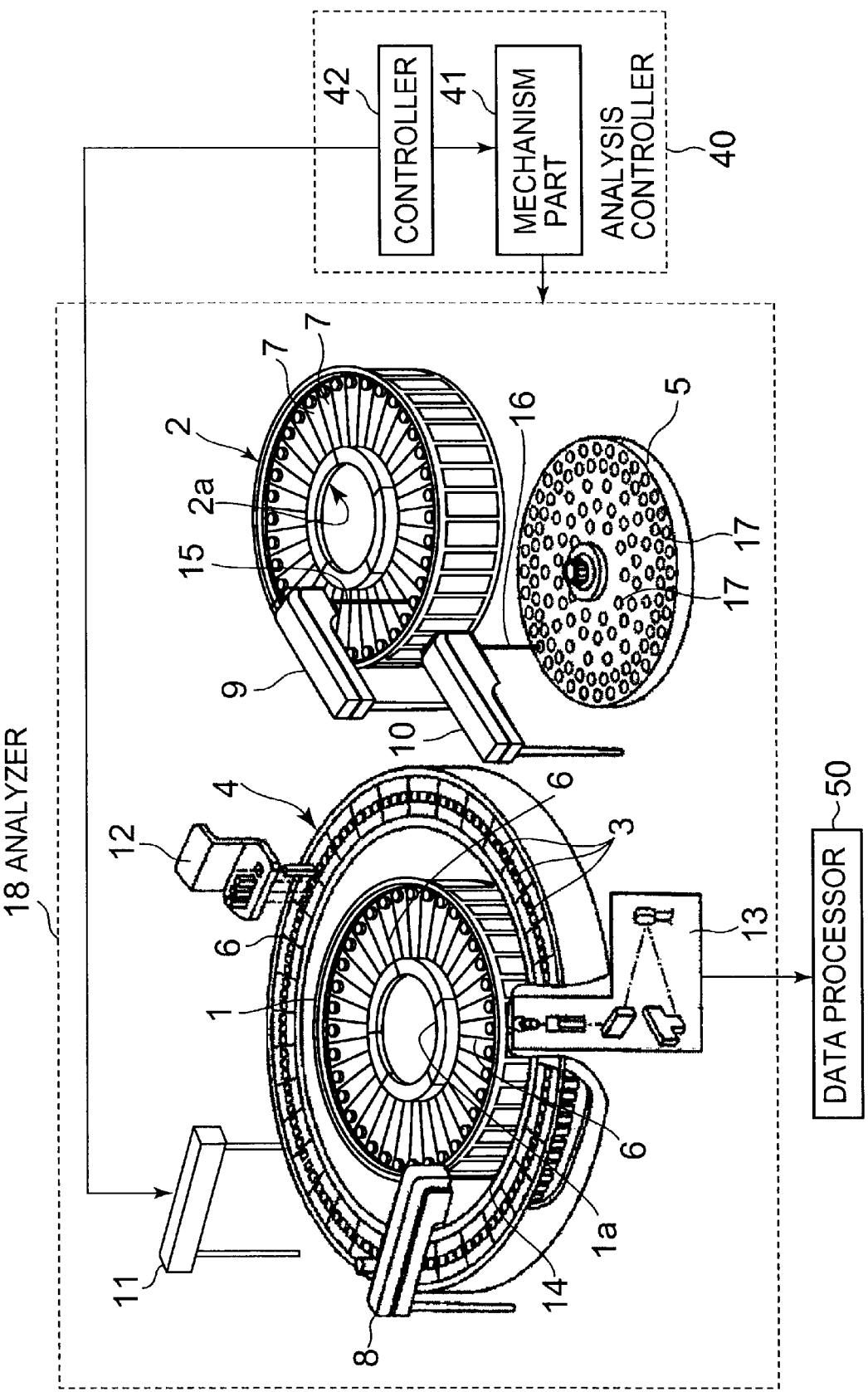
FIG. 2 is a perspective view showing the configuration of an analyzer in the embodiment of the present invention.

FIG. 2 is a perspective view showing the configuration of the analyzer 18. The analyzer 18 is provided with: a sample container 17 configured to house samples such as the standard samples and the test samples; a disk sampler 5 configured to hold the sample container 17 housing the samples so as to be rotatable; a sample dispensing probe 16 configured to execute a dispensing operation of sucking the sample from the sample container 17 and discharging it to a reaction container 3 in every analysis cycle; and a sample dispensing arm 10 configured to hold the sample dispensing probe 16 so as to be rotatable and vertically movable.

Further, the analyzer 18 is provided with: a reagent container 6 configured to house a first reagent that reacts with a component of each of the test items included in the sample; a first reagent storage 1 in which a rack 1a for rotatably holding the reagent container 6 housing the first reagent is stored; a first reagent dispensing probe 14 configured to, in every analysis cycle, execute a dispensing operation of sucking the first reagent from the reagent container 6 in the first reagent storage 1 and discharging it to the reaction container 3 into which the sample has been dispensed; and a first reagent dispensing arm 8 configured to hold the first reagent dispensing probe 14 so as to be rotatable and vertically movable.

Furthermore, the analyzer 18 is provided with: a sample container 7 configured to house a second reagent paired with the first reagent; a second reagent storage 2 in which a rack 2a for rotatably holding the reagent container 7 housing the second reagent is stored; a second reagent dispensing probe 15 configured to, in every analysis cycle, execute a dispensing operation of sucking the second reagent from the reagent container 7 in the second reagent storage 2 and discharging it to the reaction container 3 into which the sample and the first reagent have been dispensed; and a second reagent dispensing arm 9 configured to hold the second reagent dispensing probe 15 so as to be rotatable and vertically movable.

Furthermore, the analyzer 18 is provided with: a reaction disk 4 configured to rotationally move, by a predetermined angle $\theta 1$, a plurality (m pieces) of reaction containers 3 arranged at equal intervals on the circumference in every analysis cycle and then stop them; a stirring part 11 configured to stir, in every analysis cycle, a first mixture composed of the sample and the first reagent discharged into the reaction container 3 or a second mixture composed of the sample, the first reagent, and the second reagent; a photometric part 13 configured to measure the first mixture or the second mixture within the reaction container 3; and a cleaning unit 12 configured to hold, so as to be vertically movable, a cleaning nozzle for sucking the first mixture or the second mixture after measurement in the reaction container 3 and cleaning the inside of the reaction container 3, and a drying nozzle for drying the inside of the reaction container 3.

The photometric part 13 applies light to the rotationally moving reaction container 3 at a photometric position, converts the light transmitted through the mixture containing the standard sample into absorbance to generate the standard sample data, and thereafter outputs it to the data processor 50. Moreover, the photometric part 13 converts the light transmitted through the mixture containing the test sample into absorbance to generate the test sample data, and thereafter outputs it to the data processor 50. The reaction container 3, sample dispensing probe 16, first and second reagent dispensing probes 14 and 15 and stirring part 11 after measurement, i.e., the respective units having contacted liquids such as the sample, the first reagent, the second reagent, the first mixture and the second mixture, are cleaned and thereafter used in measurement again.

The analysis controller 40 is provided with a mechanism part 41 having mechanisms for driving the respective units of the analyzer 18, and a controller 42 configured to drive the respective mechanisms of the mechanism part 41 and control the respective units of the analyzer 18.

The mechanism part 41 is provided with: mechanisms configured to rotate the rack 1a of the first reagent storage 1, the rack 2a of the second reagent storage 2, and the disk sampler 5, respectively; a mechanism configured to rotate the reaction disk 4; mechanisms configured to rotate and vertically move part of the units including the sample dispensing arm 10, first reagent dispensing arm 8, second reagent dispensing arm 9 and stirring part 11, respectively; and a mechanism configured to vertically move the cleaning unit 12.

Further, the mechanism part 41 is provided with: a mechanism configured to drive a sample dispensing pump to suck and discharge, the sample dispensing pump causing the sample dispensing probe 16 to suck and discharge the sample; mechanisms configured to drive first and second reagent pumps to suck and discharge, respectively, the first and second reagent pumps causing the first and second reagent dispensing probes 14 and 15 to suck and discharge the first and second reagents; a mechanism configured to drive a cleaning pump that sucks the first mixture or the second mixture from the cleaning nozzle of the cleaning unit 12 or that discharges and sucks a cleaning solution; a mechanism configured to drive a drying pump that sucks from the drying nozzle of the cleaning unit 12; and so on.

The data processor 50 shown in FIG. 1 is provided with: a calculator 51 configured to create a calibration curve or generate analysis data from standard sample data or test sample data outputted from the analyzer 18; and a data storage 52 configured to store the calibration curve created by the calculator 51, the analysis data generated thereby, etc.

The calculator 51 creates a calibration curve from the standard sample data of each test item outputted from the photometric part 13 of the analyzer 18, and stores it into the data storage 52 and also outputs it to the output part 60. Moreover, the calculator 51 reads out a calibration curve of a test item corresponding to the test sample data outputted from the photometric part 13 of the analyzer 18, from the data storage 52.

Next, the calculator 51 generates analysis data such as the density and active value of a test item component from the test sample data by using the calibration curve having been read out, and stores the generated analysis data into the data storage 52 and also outputs it to the output part 60.

The data storage 52 is provided with a hard disk, etc. The data storage 52 stores the calibration curve outputted from the calculator 51 for every test item, and stores the analysis data of the respective test items outputted from the calculator 51 for every test sample.

The output part 60 is provided with a printing part 61 configured to print out the calibration curve, the analysis data, etc., outputted from the data processor 50, and a display 62 configured to display them. The printing part 61 is provided with a printer, etc. The printing part 61 prints out the calibration curve, the analysis data, etc., outputted from the data processor 50 to printing sheets in accordance with preset formats.

The display 62 is provided with a monitor such as a CRT and a liquid crystal display. The display 62 displays the calibration curve or analysis data outputted from the data processor 50. The display 62 also displays: an analysis condition setting screen for setting analysis conditions such as the amounts of the sample, first reagent and second reagent and the wavelength for each test item; a subject information setting screen for setting the ID and name of a subject, etc.; a measurement item selecting screen for selecting a test item to measure for each test sample; and so on.

The operation part 70 is provided with an input device such as a keyboard, a mouse, a button, and a touch screen. The operation part 70 is used for inputting subject information such as a subject ID and a subject name, a test item to measure for each test sample, and the like.

The system controller 80 is provided with a CPU and a memory circuit. The system controller 80 stores a command signal supplied from the operation part 70, analysis conditions for each test item, the subject information, and information such as a test item to measure for each test sample. Then, the system controller 80 controls the entire system based on these information.

Next, with reference to FIGS. 1 to 9, the configuration and operation of the stirring part 11 in the analyzer 18 will be described.

Figure 3:
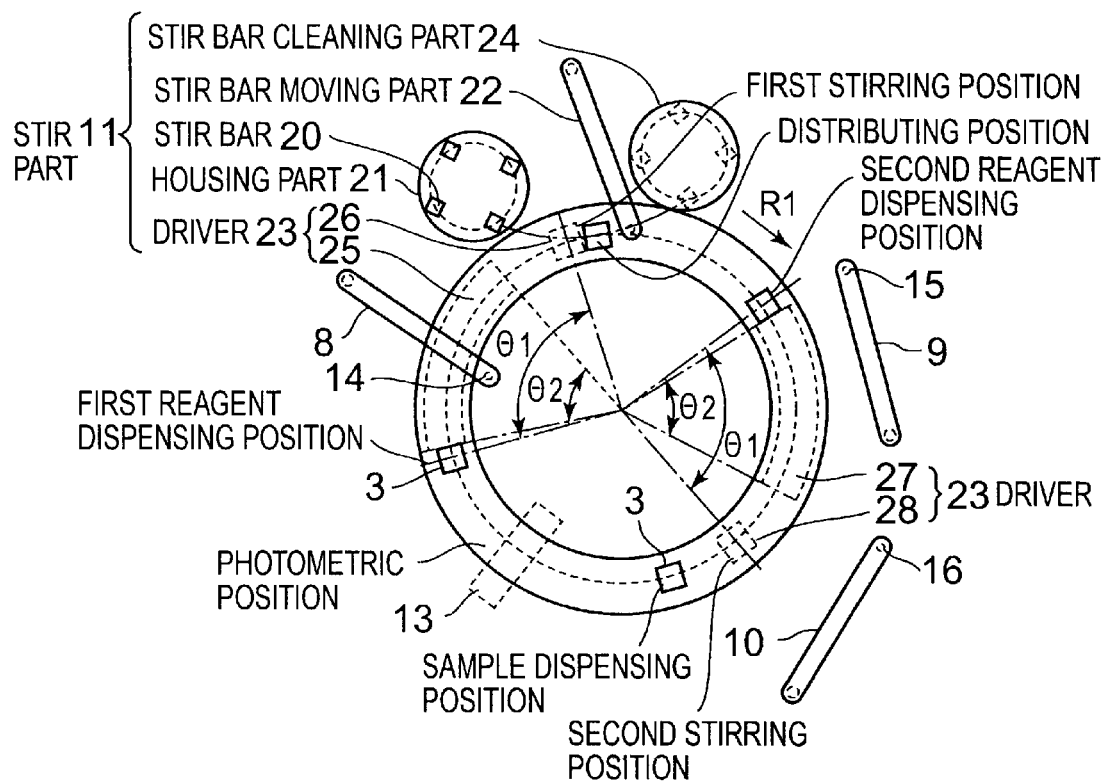
FIG. 3 is a view showing the configuration of a stir piece in the embodiment of the present invention.

FIG. 3 is a top view showing the configuration of the stirring part 11. The stirring part 11 is placed on the outer periphery of the reaction disk 4 of the analyzer 18. The stirring part 11 is provided with a stir piece 20 for stirring the first mixture or the second mixture in the reaction container 3, a housing part 21 that houses the stir piece 20, a stir piece moving part 22 for moving the stir piece 20 housed by the housing part 21 into the reaction container 3, a driver 23 for driving the stir piece 20 in the reaction container 3 to stir the first mixture or the second mixture, and a stir piece cleaning part 24 for cleaning the stir piece 20 having been for stirring the first mixture or the second mixture.

Figure 4:
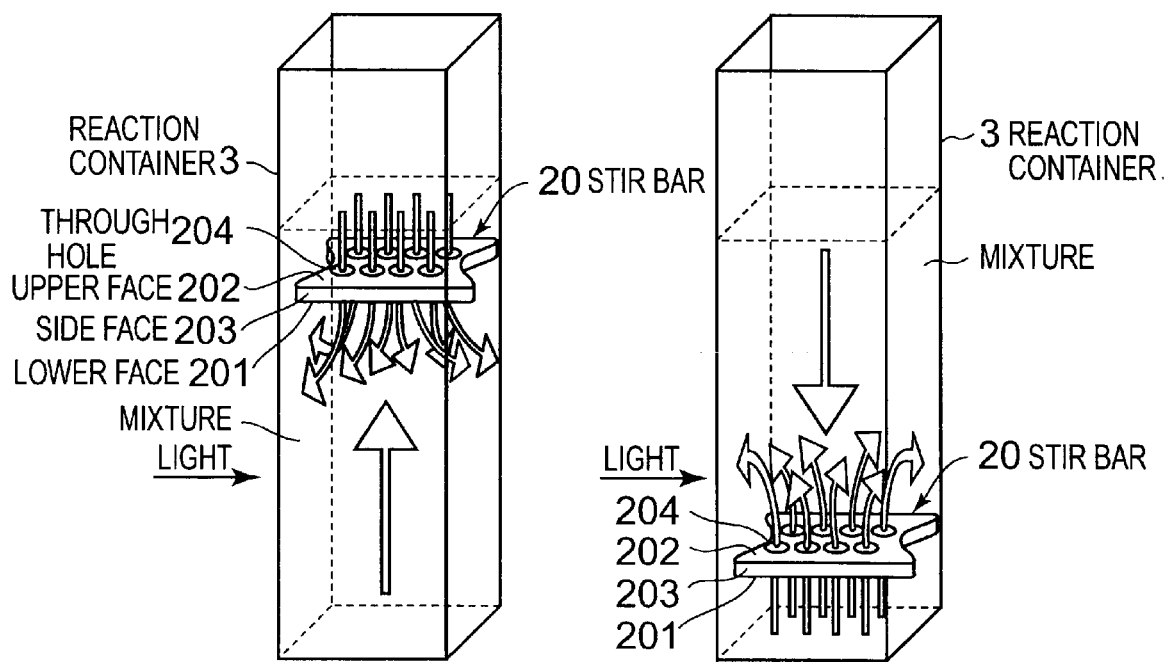
FIG. 4 is a view showing an example of the stir piece in the embodiment of the present invention.

FIG. 4 is a view showing an example of the stir piece 20 in the reaction container 3. For example, the stir piece 20 is a permanent magnet that indicates either the north pole or the south pole on a lower face 201 and the other pole on an upper face 202 and that can vertically move in the reaction container 3. The stir piece 20 is coated with a material having high chemical resistance and small frictional coefficient, such as polytetrafluoroethylene.

The lower face 201 and the upper face 202 are similar in shape, which are slightly smaller than the bottom face of the inside of the reaction container 3 that is open-topped and formed into a hollow quadrangular column. A part of a side face 203 facing the inner wall of the reaction container 3 transmitting light is constricted so as not to contact a light-transmitting part of the inner wall. Moreover, the side face 203 has a specified height so that the lower face 201 and the upper face 202 cannot be reversely positioned in the reaction container 3, and the stir piece 20 is housed in the reaction container 3 so as to be vertically movable. Besides, a plurality of piercing holes 204 that pierce the lower face 201 and the upper face 202 are formed so that the first mixture or the second mixture can flow from either the lower side of the lower face 201 or the upper side of the upper face 202 to the other and can be stirred when the stir piece 20 vertically moves in the reaction container 3.

Figure 5:
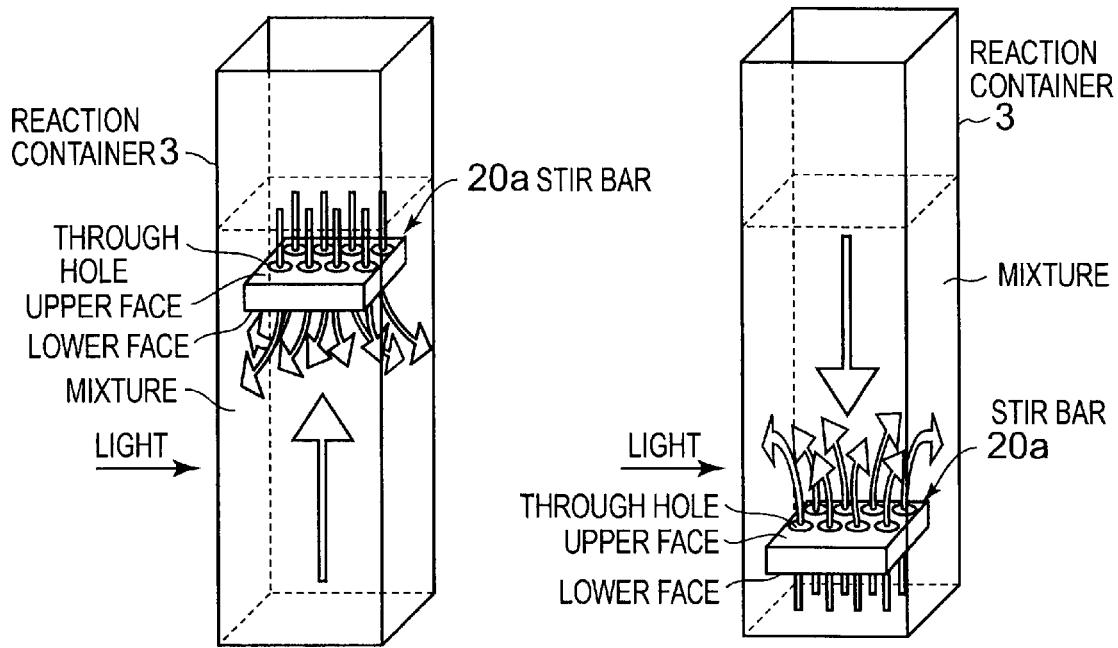
FIG. 5 is a view showing another example of the stir piece in the embodiment of the present invention.
Figure 6:
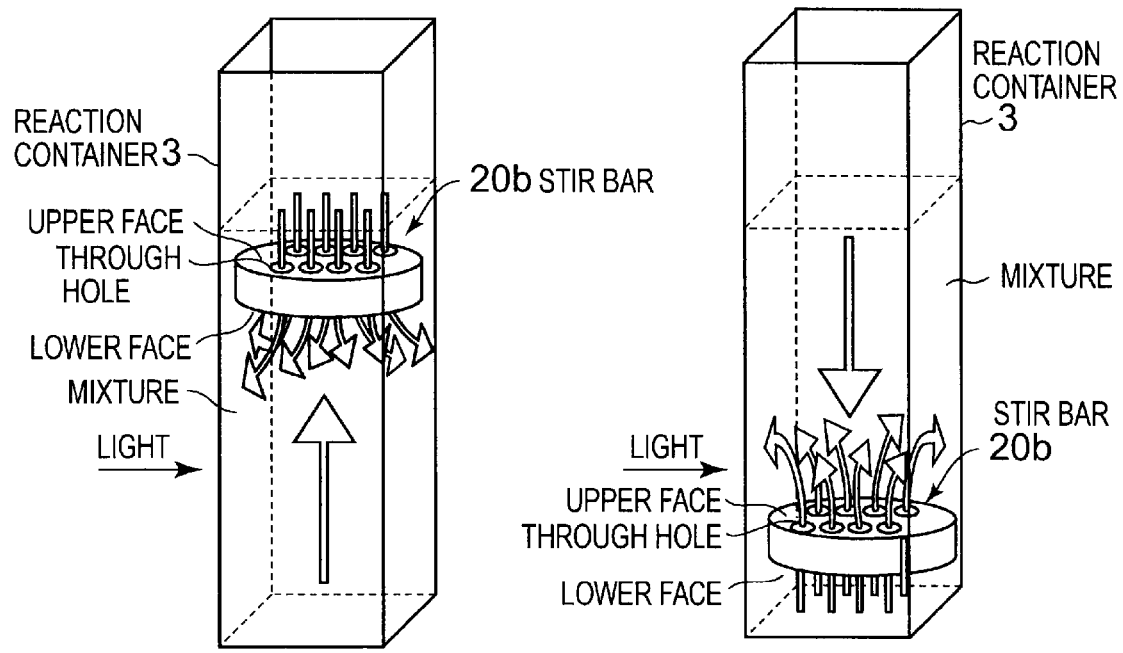
FIG. 6 is a view showing another example of the stir piece in the embodiment of the present invention.

The configuration of the stir piece is not limited to the above example, and the stir piece may be a rectangular stir piece 20a whose lower and upper faces are along the bottom face of the inside of the reaction container 3 as shown in FIG. 5. Moreover, as shown in FIG. 6, the stir piece may be a stir piece 20b whose lower and upper faces are circular. Besides, the stir piece may be a stir piece whose lower and upper faces have similar shapes slightly smaller than the bottom face of the inside of the reaction container that is open-topped and formed into a hollow cylindrical column or polygonal column other than quadrangular column.

The housing part 21 of FIG. 3 houses a plurality of stir pieces 20 with upper faces 202 facing above so as to be rotatable. Moreover, the stir piece 20 cleaned in the stir piece cleaning part 24 is dried.

FIG. 7 is a view showing the configuration of the stir piece moving part 22. The stir piece moving part 22 is controlled by the analysis controller 40. The stir piece moving part 22 includes an absorption/desorption probe 221 that absorbs and desorbs the stir piece 20 at the lower end thereof, and a moving arm 222 that holds the upper end of the absorption/desorption probe 221 so as to be vertically movable and rotatable.

Figure 8A:
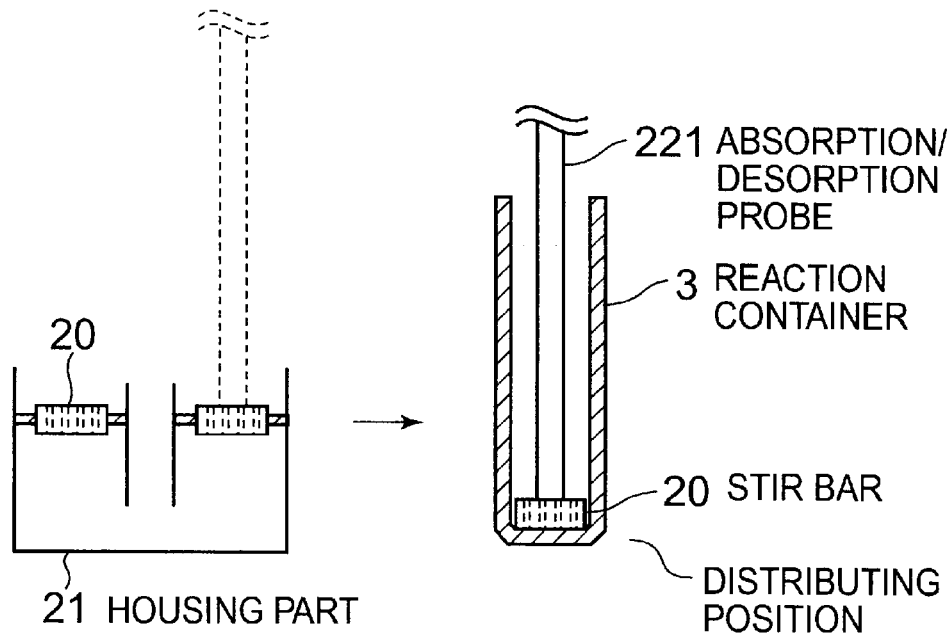
FIGS. 8A and 8B are views showing movement of the stir piece by the stir piece moving part in the embodiment of the present invention.

For example, the absorption/desorption probe 221 has an electromagnet in the lower end thereof. As shown in FIG. 8A, the absorption/desorption probe 221 moves into the housing part 21, approaches and absorbs the upper face 202 of an unused or dried stir piece 20 by electric power supplied to the electromagnet from the controller 42 of the analysis controller 40, and thereafter desorbs the absorbed stir piece 20 within the reaction container 3 stopping at a distributing position as the controller 42 stops supplying electric power to the electromagnet.

Figure 8B:
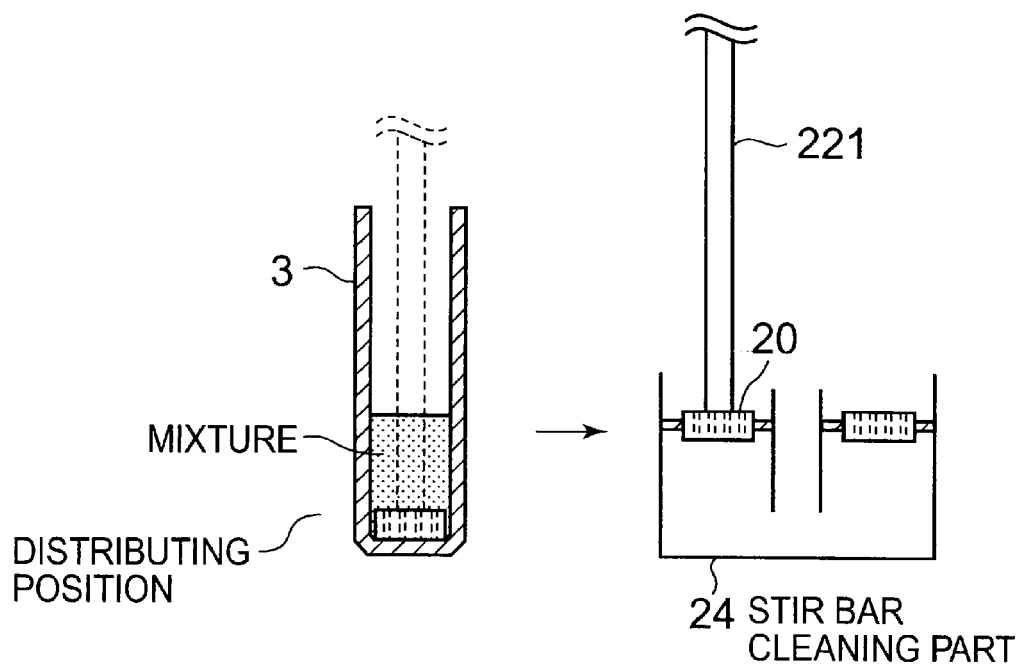

Further, as shown in FIG. 8B, the absorption/desorption probe 221 moves into the reaction container 3 after measurement stopping at the distributing position, absorbs the stir piece 20 by electric power supplied to the electromagnet, and thereafter desorbs the absorbed stir piece 20 within the stir piece cleaning part 24 as the controller 42 stops supplying electric power to the electromagnet. In the stir piece cleaning part 24, a mixture adhering to the stir piece 20 is washed away by using alkaline detergent, acid detergent, cleaning solution containing surface active agent, etc., or pure water. The mixture may be washed away by simultaneously using ultrasonic cleaning. Furthermore, the absorption/desorption probe 221 moves into the stir piece cleaning part 24, absorbs the cleaned stir piece 20, and thereafter desorbs the absorbed stir piece 20 within the housing part 21.

The stir piece 20 may be moved in a state where the plurality of piercing holes 204 or the margins of the stir piece 20 are sandwiched by an absorption/desorption probe provided with a robot arm mechanism near the lower end thereof.

The moving arm 222 is vertically moved and rotated by the mechanism part 41 of the analysis controller 40 to move the absorption/desorption probe 221 from the inside of the housing part 21 to the inside of the reaction container 3 stopping at the distributing position. Moreover, the moving arm 222 moves it from the inside of the reaction container 3 stopping at the distributing position to the inside of the stir piece cleaning part 24. Besides, the moving arm 222 moves it from the inside of the stir piece cleaning part 24 to the inside of the housing part 21.

The driver 23 of FIG. 3 is provided with: a first driver 25 that drives the stir piece 20 in the reaction container 3 to stir the first mixture while the reaction container 3 into which the first reagent has been dispensed at a first reagent dispensing position is rotationally moving in an arrow R1 direction; and a second driver 26 that drives the stir piece 20 in the reaction container 3 to stir the first mixture while the reaction container 3 after stir by the first driver 25 is stopping at a first stirring position. Moreover, the driver 23 is provided with: a first driver 27 that drives the stir piece 20 in the reaction container 3 to stir the second mixture while the reaction container 3 into which the second reagent has been dispensed at a second reagent dispensing position is rotationally moving; and a second driver 28 that drives the stir piece 20 in the reaction container 3 to stir the second mixture while the reaction container 3 after stir by the first driver 27 is stopping at a second stirring position.

FIG. 9 is a view showing the configuration of the first and second drivers 25 and 26. The first driver 25 has: first magnets 25a1 to 25an, which are n (2<n<m) pieces of electromagnets whose ends facing up can be magnetized to the same pole as the one pole of the lower face 201 of the stir piece 20; and second magnets 25b1 to 25bn, which are n pieces of electromagnets whose ends facing up can be magnetized to the opposite pole. The first magnets 25a1 to 25an and the second magnets 25b1 to 25bn are alternately arranged, and are magnetized by electric power (direct current) supplied from the controller 42 of the analysis controller 40 at a timing when the reaction container 3 into which the first reagent has been dispensed passes over the respective magnets.

Further, the first driver 25 is arranged below an orbit on which the reaction container 3 rotationally moves, in a range of an angle θ2 included in the range of the predetermined angle θ1 between the first reagent dispensing position at which the first reagent is dispensed into the reaction container 3 by the first reagent dispensing probe 14 and the first stirring position at which the reaction container 3 stops after rotationally moving from the first reagent dispensing position in one analysis cycle, as shown in FIG. 3.

Next, with reference to FIGS. 2 to 9, the operation of stirring the first mixture within the reaction container 3 will be described.

When the reaction container 3 cleaned and dried by the cleaning unit 12 of the analyzer 18 stops at the distributing position, the stir piece moving part 22 moves the stir piece 20 in the housing part 21 to the inside of the reaction container 3. After the stir piece 20 is moved to the inside of the reaction container 3, the sample dispensing probe 16 dispenses the sample from the sample container 17 into the reaction container 3 when the reaction container 3 housing the stir piece 20 stops at a sample dispensing position. After the sample is dispensed, the first reagent dispensing probe 14 dispenses the first reagent from the reagent container 6 in the first reagent storage 1 to the inside of the reaction container 3 when the reaction container 3 housing the sample stops at the first reagent dispensing position.

The reaction container 3, into which the first reagent has been dispensed at the first reagent dispensing position, rotationally moves in the arrow R1 direction. The stir piece 20 in the reaction container 3 is repulsed by the first magnet 25a1 placed below a one-pitch position rotationally moved by one pitch from the first reagent dispensing position and is moved upward, and thereafter, is absorbed by the second magnet 25b1 placed below a two-pitch position rotationally moved by two pitches and is moved downward. Here, one pitch is equivalent to a rotation angle obtained by dividing 360 degrees by m, which is the number of the reaction containers 3.

Next, after being repulsed by the first magnet 25*a*2 placed below a three-pitch position rotationally moved by three pitches and being moved upward, the stir piece 20 is absorbed by the second magnet 25*b*2 placed below a four-pitch position rotationally moved by four pitches and is moved downward.

Furthermore, after being repulsed by the first magnet 25*an* placed below a (2*n*n−1)-pitch position rotationally moved by (2n−1) pitches and being moved upward, the stir piece 20 is absorbed by the second magnet 25*bn* placed below a 2n-pitch position rotationally moved by 2n pitches, and is moved downward, where the stir piece 20 stops.

The first driver 25 may be configured in a manner that: either the first magnets or the second magnets are lined at consecutive-two-pitch positions and the other magnets are lined at one-pitch positions or at consecutive-two-pitch positions; and then the former magnets lined at the two-pitch positions and the latter magnets lined at the one-pitch positions or at the consecutive-two-pitch positions are alternately arranged.

Thus, during the rotation movement of the reaction container 3 into which the first reagent has been dispensed at the first reagent dispensing position, it is possible to vertically move the stir piece 20 in the reaction container 3 to stir the first mixture.

The second driver 26 has a third magnet 26*a*, which is an electromagnet whose end facing up can be alternately magnetized to one pole and the other pole, i.e., the north pole and the south pole. Then, while the reaction container 3 with the first reagent dispensed is stopping at the first stirring position, the third magnet 26*a* is alternately magnetized to the one pole and the other pole by specified frequency of alternate current supplied from the controller 42, and vertically moves the stir piece 20 in the reaction container 3.

The reaction container 3 with the first reagent dispensed stops at the first stirring position after rotation movement to the 2n-pitch position. The stir piece 20 in the reaction container 3 repeatedly performs the operation of being repulsed by the third magnet 26*a* to move upward and thereafter being absorbed thereby to move downward.

It is also possible to configure so as to move the stir piece into the reaction container 3 stopping at the first stirring position from above and thereafter rotate or vibrate the moved stir piece to stir the first mixture in the reaction container 3.

Thus, it is possible to vertically move the stir piece 20 in the reaction container 3 and stir the first mixture while the reaction container 3 with the first reagent dispensed at the first reagent dispensing position is stopping after the rotation movement.

Consequently, it becomes possible to stir the first mixture in the reaction container 3 while the reaction container 3 is rotationally moving and while the reaction container 3 is stopping after the rotational movement, so that it is possible to stir the first mixture for a long time period.

The first driver 27 is arranged below the orbit on which the reaction container 3, into which the second reagent has been dispensed by the second reagent dispensing probe 15 at the second reagent dispensing position, rotationally moves, and is configured in a similar manner as the first driver 25. Therefore, a description thereof will be omitted. Then, the respective magnets composing the first driver 27 are magnetized by direct current supplied from the controller 42 at a timing when the reaction container 3 with the second reagent dispensed passes over the respective magnets. The stir piece 20 in the reaction container 3 is vertically moved to stir the second mixture.

Thus, during the rotational movement of the reaction container 3 into which the second reagent has been dispensed at the second reagent dispensing position, it is possible to vertically move the stir piece 20 in the reaction container 3 and stir the second mixture.

Since the second driver 28 is arranged below the second stirring position at which the reaction container 3 with the second reagent dispensed stops after rotationally moving and is configured similarly to the second driver 26, a description thereof will be omitted. Then, while the reaction container 3 with the second reagent dispensed is stopping at the second stirring position, the magnet composing the second driver 28 vertically moves the stir piece 20 in the reaction container 3 by specified frequency of alternate current supplied from the controller 42 to stir the second mixture.

Thus, it is possible to, while the reaction container 3 with the first reagent dispensed at the second reagent dispensing position is stopping after the rotational movement, vertically move the stir piece 20 in the reaction container 3 and stir the second mixture. Consequently, it becomes possible to stir the second mixture in the reaction container 3 while the reaction container 3 is rotationally moving and while the reaction container 3 is stopping after the rotational movement, so that it is possible to stir the second mixture for a long time period.

The stir piece cleaning part 24 shown in FIG. 3 cleans the stir piece 20 moved by the stir piece moving part 22 from the reaction container 3 containing the first mixture or the second mixture, and a part of the absorption/desorption probe 221 contacted the first mixture or the second mixture during the movement of the stir piece 20. Then, the stir piece 20 cleaned by the stir piece cleaning part 24 is moved by the stir piece moving part 22 to the housing part 21, and thereafter, is dried in the housing part 21 and used for measurement again.

The stir piece cleaning part 24 may be replaced with a stir piece collecting box so that the stir piece 20 in the reaction container 3 having been used for measurement is collected and discarded into the collecting box.

Figure 11:
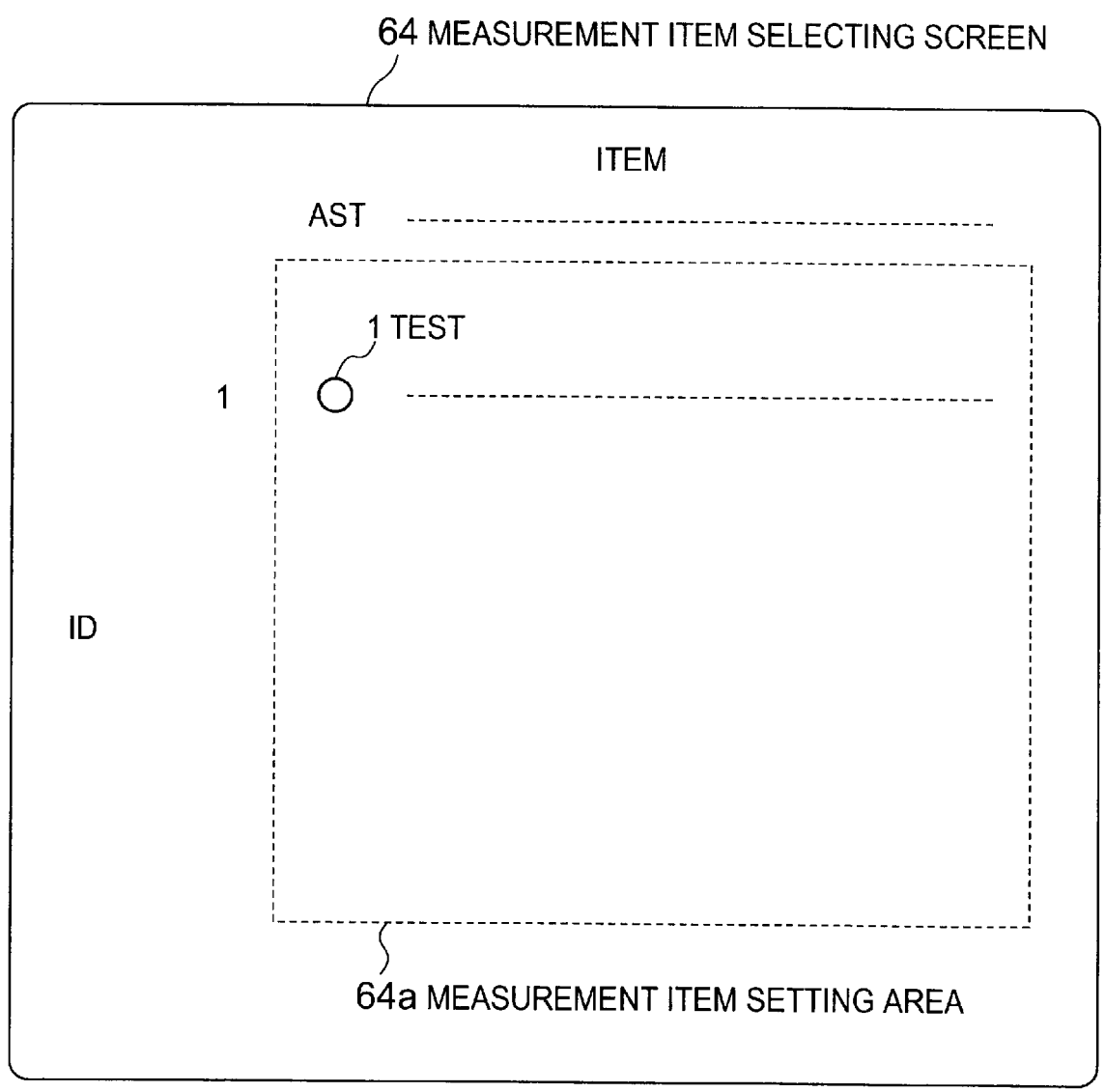
FIG. 11 is a view showing an example of a measurement item screen displayed on the display in the embodiment of the present invention.
Figure 12:
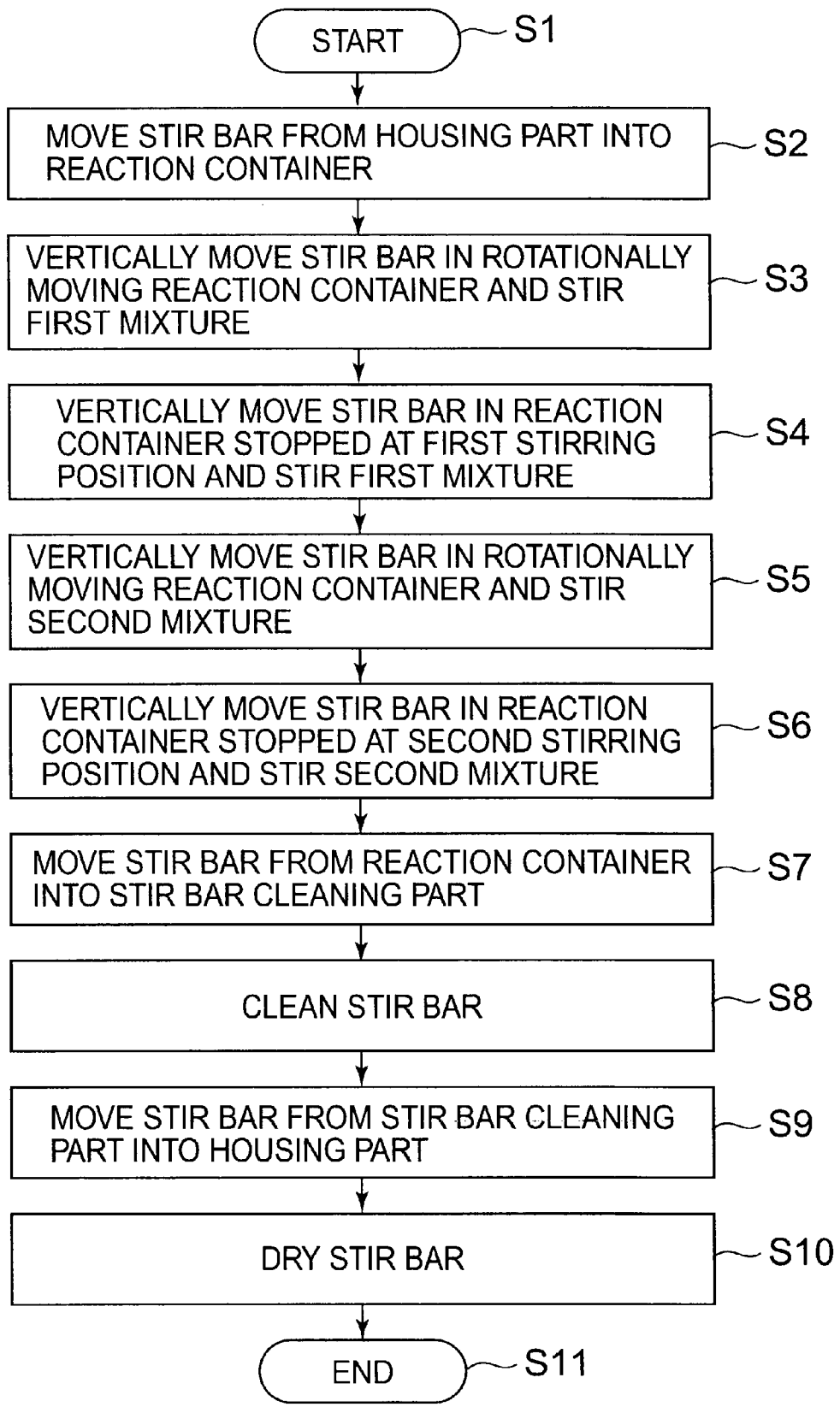
FIG. 12 is a flow chart showing the operation of the automatic analyzing apparatus according to the present invention.

With reference to FIGS. 1 to 12, an example of the operation of the automatic analyzing apparatus 100 will be described below. FIG. 10 is a view showing an example of the analysis condition setting screen displayed on the display 62. FIG. 11 is a view showing an example of the measurement item selecting screen displayed on the display 62. FIG. 12 is a flowchart showing the operation of the automatic analyzing apparatus 100.

In FIG. 10, an analysis condition setting screen 63 includes fields like "item name," "sample amount," "reagent amount," "wavelength" and "photometric point" and dialogue boxes 631 to 638 for setting analysis conditions in the respective fields. When an input operation into each of the dialogue boxes corresponding to the fields of the analysis condition setting screen 63 is performed for each test item through the operation part 70, input information on the inputted analysis conditions for each test item is stored into the memory circuit of the system controller 80.

In the "item name" field, the name of a desired test item is selected and set from among a plurality of test items set in advance. For example, through an operation of selecting and inputting aspartate aminotransferase as the name of a test item, "AST," which is the abbreviated name of aspartate aminotransferase, is displayed in the dialogue box 631.

In the "sample amount" field, the amount of a sample dispensed into the reaction container 3 at the time of measurement of the test item set in the "item name" field is set. For example, through an operation of inputting 5 μL as the sample amount, "5" is displayed in the dialogue box 632.

In the "reagent amount" field, a "first reagent" field and a "second reagent" field are displayed. In a case where a reagent used for measurement of the test item set in the "item name" field is a one-reagent type, the amount of the first reagent dispensed into the reaction container 3 is set in the "first reagent" field. In the case of a two-reagent type, the amounts of the first and second reagents dispensed into the reaction container 3 are set in the "first reagent" field and the "second reagent" field. Then, through an operation of inputting 150 μL as the amount of the first reagent of the two-reagent type, "150" is displayed in the dialogue box 633. Moreover, through an operation of inputting 50 μL as the amount of the second reagent, "50" is displayed in the dialogue box 634.

In the "wavelength" field, a "wavelength 1" field and a "wavelength 2" field are displayed, and a wavelength appropriate for the kind of reaction of the test item set in the "item name" field is set.

One wavelength or two different wavelengths are selected and set from among wavelengths set in advance.

Then, for example, through an operation of selecting and inputting 340 nm, which is appropriate for the kind of reaction of the test item set in the "item name" field, into the "wavelength 1" field, "340" is displayed in the dialogue box 635. Moreover, for example, through an operation of selecting and inputting 380 nm into the "wavelength 2" field, "380" is displayed in the dialogue box 636.

In the "photometric point" field, for example, through an operation of selecting and inputting twentieth to twenty-ninth photometric points as the timings for measuring a mixture for the test item set in the "item name" field, "20" is displayed in the dialogue box 637, and "29" is displayed in the dialogue box 638.

Here, for example, a time when the reaction container 3 with the first reagent dispensed rotationally moves and first passes through a photometric position between the sample dispensing position and the first reagent dispensing position as shown in FIG. 3 is defined as a first photometric point. Then, analysis data is generated based on ten pieces of test sample data generated by the photometric part 13 through measurement at the twentieth to twenty-ninth points, which are points that the reaction container 3 with the second mixture composed of the test sample, the first reagent and the second reagent passes through the photometric position for the twentieth to twenty-ninth times.

FIG. 11 is a view showing an example of the measurement item selecting screen displayed on the display 62. A measurement item selecting screen 64 includes: an "ID" field for displaying, for example, subject IDs of test samples set in the subject information setting screen; an "item" field for displaying the test item set in the analysis condition setting screen 63 of FIG. 10; and a measurement item setting area 64a for selecting an test item measured for each of the subject IDs displayed in the "ID" field from the "item" field.

In the "ID" field, for example, a subject ID "1" set in the subject information setting screen is displayed. Moreover, in the "item" field, for example, a test item name "AST" set in the analysis condition setting screen 63 is displayed.

In the measurement item setting area 64a, "○" is displayed in an area of the test item name selected in the "item" field corresponding to the subject ID selected in the "ID" field, whereas "." is displayed in an unselected area. In a case where the test item name "AST" is selected for the sample ID "1" through the operation part 70, "○" equivalent to a first test is displayed in the area of "AST" of the "item" field corresponding to "1" of the "ID" field in the measurement item setting area 64a.

(Operation)

Next, a series of operations by the automatic analyzing apparatus 100 according to the embodiment of the present invention will be described with reference to FIG. 12. FIG. 12 is a flowchart showing the operation of the automatic analyzing apparatus 100. In the memory circuit of the system controller 80, analysis conditions set in the analysis condition setting screen 63 and information on a test item for each test sample selected in the measurement item selecting screen 64 are stored. Moreover, information on reagent properties such as viscosity and bubbliness of the first reagent and the second reagent set in advance for each test item is stored.

After the sample container 17 in which the test sample of the subject ID set in the subject information setting screen is installed in the disk sampler 5 of the analyzer 18, when a measurement start operation for measuring the test sample is performed through the operation part 70, the automatic analyzing apparatus 100 starts the operation (step S1).

The system controller 80 instructs measurement of the test sample to the controller 42 of the analysis controller 40. The analyzer 18 is controlled by the controller 42 to measure the test item of the test sample selected and set in the measurement item selecting screen 64, based on analysis conditions for each test item set in the analysis condition setting screen 63. When the reaction container 3 cleaned and dried in the cleaning unit 12 stops at the distributing position, the stir piece moving part 22 of the stir part 11 in the analyzer 18 moves the stir piece 20 from the housing part 21 into the reaction container 3 (step S2).

When the reaction container 3 in which the stir piece 20 is housed stops at the sample dispensing position, the sample dispensing probe 16 dispenses the test sample corresponding to the test item of a first test from the sample container 17 into the reaction container 3. When the reaction container 3 into which the test sample has been dispensed stops at the first reagent dispensing position, the first reagent dispensing probe 14 dispenses the first reagent for the test item of the first test from the reagent container 6 of the first reagent storage 1 into the reaction container 3.

The reaction container 3 with the first reagent dispensed at the first reagent dispensing position rotationally moves in the R1 direction.

The first driver 25 of the stirring part 11 vertically moves the stir piece 20 in the rotationally moving reaction container 3 and stirs the first mixture (step S3).

The second driver 26 vertically moves the stir piece 20 in the reaction container 3 stopping at the first stirring position after the rotational movement and stirs the first mixture (step S4).

The reaction container 3 with the first reagent dispensed repeats the rotational movement and the stoppage, and stops at the second reagent dispensing position after a specified time. The second reagent dispensing probe 15 dispenses the second reagent for the test item of the first test from the reagent container 7 of the second reagent storage 2 into the reaction container 3 stopping at the second reagent dispensing position. The reaction container 3 with the second reagent dispensed rotationally moves in the R1 direction. The first driver 27 vertically moves the stir piece 20 in the rotationally moving reaction container 3 and stirs the second mixture (step S6).

The second driver 28 vertically moves the stir piece 20 in the reaction container 3 stopping at the second stirring position after rotationally moving and stirs the second mixture (step S6).

Based on the previously set test items and the analysis conditions such as the sample amount, the first reagent amount and the second reagent amount set in the analysis condition setting screen 63, it is possible to vary the level of a direct current supplied to the driver 23, the level of an alternate current, the frequency of the alternate current, the time to supply electric power and the rotation speed of the reaction container 3. For example, in a case where the viscosity of the first reagent or the second reagent of the previously set test item is higher than normal viscosity, it is possible to supply an electric current larger than that for a reagent with the normal viscosity to the first and second drivers 25, 26 or the first and second drivers 27, 28 and cause the stir piece 20 to work with stronger force, and thereby more uniformly stir the first mixture or the second mixture in the reaction container 3 corresponding to the test item.

Further, for example, in a case where the first reagent or the second reagent of the previously set test item bubbles more easily than a normal reagent, it is possible to supply an electric current smaller than that for the normal reagent to the first and second drivers 25, 26 or the first and second drivers 27, 28 and cause the stir piece 20 to work with weaker force, and thereby suppress bubbling of the first mixture or the second mixture in the reaction container 3 corresponding to the test item.

Consequently, it is possible to prevent the second mixture from being insufficiently mixed when the second reagent is dispensed into the bubbling first reagent due to the bubbliness of the first mixture.

Moreover, it is possible to suppress bubbling up to the upper part in the reaction container 3 that the cleaning unit 12 cannot reach to clean.

After the second mixture is stirred, the photometric part 13 measures the second mixture in the reaction container 3 at the photometric point set in the analysis condition setting screen 63 that is a photometric position of the reaction container 3. Then, the generated test sample data is outputted to the calculator 51 of the data processor 50. The stir piece 20 when passing through the photometric position is sunk to the bottom inside the reaction container 3 that is not included in a region of a path of light emitted from the photometric part 13.

The stir piece moving part 22 moves the stir piece 20 after measurement from the reaction container 3 into the stir piece cleaning part 24 (step S7).

The stir piece cleaning part 24 cleans the stir piece 20 after measurement moved by the stir piece moving part 22 (step S8).

The stir piece moving part 22 moves the stir piece 20 after cleaning from the stir piece cleaning part 24 into the housing part 21 (step S9).

The housing part 21 dries the cleaned stir piece 20 moved by the stir piece moving part 22 (step S10).

The calculator 51 reads out a previously created calibration curve from the data storage 52. Next, the calculator 51 generates analysis data from test sample data outputted from the photometric part 13 by using the calibration curve having been read out, and stores the generated analysis data into the data storage 52 and also outputs it to the output part 60.

The cleaning unit 12 absorbs the mixture after measurement in the reaction container 3, and cleans and dries the inside of the reaction container 3. At the point of time that the cleaning and drying of the reaction container 3 is finished and the analysis data of the test item of the sample ID "1" is outputted to the output part 60, the automatic analyzing apparatus 100 ends the operation (step S11).

According to the embodiment of the present invention described above, during the rotation movement of the reaction container 3 into which the first reagent has been dispensed at the first reagent dispensing position and in which the stir piece 20 and the sample are housed, it is possible to vertically move the stir piece 20 in the reaction container 3 by the first driver 25 and stir the first mixture. Moreover, while the reaction container 3 with the first reagent dispensed is stopping after rotationally moving, it is possible to vertically move the stir piece 20 in the reaction container 3 by the second driver 26 and stir the first mixture. Consequently, it is possible to stir the first mixture in the reaction container 3 for a long time period during the rotation movement and the stoppage of the reaction container 3.

Further, during the rotation movement of the reaction container 3 into which the second reagent has been dispensed at the second reagent dispensing position, it is possible to vertically move the stir piece 20 in the reaction container 3 by the first driver 27 and stir the second mixture. Moreover, during the stoppage of the reaction container 3 with the second reagent dispensed after the rotational movement, it is possible to vertically move the stir piece 20 in the reaction container 3 by the second driver 28 and stir the second reagent. Consequently, it is possible to stir the second mixture in the reaction container 3 for a long time period during the rotation movement and the stoppage of the reaction container 3.

Furthermore, based on the previously set test items and the analysis conditions such as the sample amount, the first reagent amount and the second reagent amount set in the analysis condition setting screen 63, it is possible to vary the level of a direct current supplied to the driver 23, the level of an alternate current, the frequency of the alternate current, the time to supply, the rotation speed of the reaction container 3, etc.

Accordingly, it becomes possible to increase the stir performance, whereby it is possible to prevent deterioration of analysis data due to insufficient stir.

The drivers 25 to 28 may be surrounded with a magnetic shield material having high magnetic permeability. By passing a magnetic line through the inside of the shield member, it becomes possible to decrease the influence of the magnetic line on the surroundings of the drivers.

Further, the stir piece may be driven by the action of the electric field. For example, the lower face of the stir piece is positively charged (plus) or negatively charged (minus). Then, the stir piece is driven upward and downward alternately by a driver disposed below the reaction container. The driver has an electrode having a plane formed so as to be capable of facing the reaction case, and the driver moves the stir piece relatively to the reaction container so that the electrode indicates either plus or minus to draw the stir piece downward and indicates the other to repulse the stir piece upward.

What is claimed is:
1. An automatic analyzing apparatus, comprising:
a reaction container having an open top and shaped as a polygonal column, the reaction container housing a mixture of a test sample and a reagent;
a stir piece housed so as to be vertically movable in a reaction container, the stir piece being a permanent magnet in a form of a plate;
a reaction container moving part configured to move the reaction container housing the stir piece and the mixture;

a photometric part configured to apply light to the reaction container and measure light transmitted through the mixture in the reaction container;

a first driver arranged below the reaction container and along the path of the reaction container moving part, the first driver including a plurality of magnets arranged in adjacent locations such that opposite polarities of each magnet face the bottom of the reaction container along the path of the reaction container moving part thereby stirring the mixture by alternately driving the stir piece in the reaction container upward and downward from outside the reaction container without contacting the stir piece during movement of the reaction container by the reaction container moving part: and a second driver arranged below the reaction container and including an electromagnet, a polarity of which changes at a position facing the reaction container, the second driver being configured to move the stir piece in the reaction container alternately upward or downward by changing the polarity of the electromagnet when the reaction container stops to stir the mixture, wherein a lower face and an upper face of the stir piece have similar shapes smaller than a bottom face of the inside of the reaction container, and a middle portion on a side face of the stir piece where light from the photometric part enters is contracted toward a center portion of the stir piece.

2. The automatic analyzing apparatus according to claim 1, further comprising:

at least one piercing hole that pierces the lower face and the upper face so that the mixture in the reaction container can flow from a lower side of the lower face to an upper side of the upper face and vice versa when the stir piece vertically moves in the reaction container.

3. The automatic analyzing apparatus according to claim 1, further comprising:

a probe configured to detachably hold the stir piece; and a movement arm configured to hold an upper end of the probe, and move the stir piece held by a lower end of the probe to at least into the reaction container.

4. The automatic analyzing apparatus according to claim 3, wherein the probe includes an electromagnet at the lower end to hold the stir piece.

5. The automatic analyzing apparatus according to claim 4, further comprising:

a mechanism configured to drive the movement arm; and a controller configured to control the probe, wherein the controller is configured to supply electric power to the electromagnet to attach the stir piece to the probe, and stop supplying the electric power to detach the stir piece from the probe.

\* \* \* \* \*